US00PP14589P29

(12) United States Plant Patent
Koppe

(10) Patent No.: US PP14,589 P2
(45) Date of Patent: Mar. 9, 2004

(54) BEGONIA PLANT NAMED 'BORIASKO'

(50) Latin Name: *Begonia×hybrida*
Varietal Denomination: Boriasko

(75) Inventor: Lubbertus H. Koppe, Ermelo (NL)

(73) Assignee: Koppe Veredeling B.V., Ermelo (NL)

( * ) Notice: Subject to any disclaimer, the term of this patent is extended or adjusted under 35 U.S.C. 154(b) by 0 days.

(21) Appl. No.: 10/396,531

(22) Filed: Mar. 25, 2003

(51) Int. Cl.[7] ..... A01H 5/00
(52) U.S. Cl. ..... Plt./348
(58) Field of Search ..... Plt./348

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Begonia plant named 'Boriasko', characterized by its upright and rounded plant habit; double flowers that are light red and pink in color and held above and beyond the foliage; and excellent postproduction longevity.

1 Drawing Sheet

Botanical classification/cultivar designation: Begonia× hybrida cultivar Boriasko.

BACKGROUND OF THE INVENTION

The present Invention relates to a new and distinct cultivar of Begonia plant, botanically known as *Begonia× hiemalis*, commercially known as Elatior Begonia, and hereinafter referred to by the name 'Boriasko'.

The new Begonia was discovered by the Inventor in a controlled environment in Ermelo, The Netherlands, in June, 2000, as a naturally-occurring whole plant mutation of *Begonia×hiemalis* 'Barkos', disclosed in U.S. Plant Pat. No. 9,523. The new Begonia was observed as a single flowering plant within a population of flowering plants of the cultivar Barkos. The selection of this plant was based on its unique flower coloration.

Asexual reproduction of the new Begonia by cuttings taken in a controlled environment in Ermelo, The Netherlands, has shown that the unique features of this new Begonia are stable and reproduced true to type in successive generations.

SUMMARY OF THE INVENTION

The cultivar 'Boriasko' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Boriasko'. These characteristics in combination distinguish 'Boriasko' as a new and distinct Begonia cultivar:

1. Upright and rounded plant habit.
2. Double flowers that are light red and pink in color and held above and beyond the foliage.
3. Excellent postproduction longevity.

Plants of the new Begonia are most similar to plants of the parent cultivar Barkos; however plants of the new Begonia differ from plants of the cultivar Barkos primarily in flower color as plants of the cultivar Barkos have red-colored flowers.

Plants of the new cultivar differ primarily from plants of the cultivar Bazan, disclosed in U.S. Plant Pat. No. 11,343, in flower color as plants of the cultivar Bazan have pink-colored flowers.

BRIEF DESCRIPTION OF THE PHOTOGRAPHS

The accompanying colored photographs illustrate the overall appearance of the new Begonia, showing the colors as true as it is reasonably possible to obtain in colored reproductions of this type. Colors in the photographs may differ slightly from the color values cited in the detailed botanical description which accurately describe the colors of the new Begonia.

The photograph at the top of the sheet comprises a side perspective view of a typical flowering plant of 'Boriasko'.

The photograph at the bottom of the sheet is a close-up view of typical flowers of 'Boriasko'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Ermelo, The Netherlands, under commercial practice in a glass-covered greenhouse. Average day and night temperatures were about 20° C. during the first three to four weeks then lowered to an average day and night temperature of 19° C. until flowering. Four weeks after planting rooted cuttings in 12-cm containers, one week of long nyctoperiods of 16 hours was given followed by short nyctoperiods of eight hours until flowering. Plants were about four months old when the photographs and description were taken. Measurements and numerical values represent averages for typical flowering plants.

Botanical classification: *Begonia×hiemalis* cultivar Boriasko.

Commercial classification: Elatior Begonia.

Parentage: Naturally-occurring whole plant mutation of *Begonia×hiemalis* cultivar Barkos, disclosed in U.S. Plant Pat. No. 9,523.

Propagation:

*Type.*—Cuttings.

*Time to develop roots.*—About 40 days at temperatures of 20 to 22° C.

*Root description.*—Fine, fibrous, well-branched and spreading. Plants of the new Begonia have not been observed to form tubers.

Plant description:

*Plant form.*—Upright and rounded plant habit; mounded inverted triangle; freely branching with good stem and stem base strength. Flowers are double and abundant.

*Growth habit.*—Moderate growth rate, vigorous. Suitable for 12 to 15-cm containers. Under optimal environmental and cultural conditions, usually about four months are required to produce proportional 13-cm potted plants from cuttings. Vegetative shoots are formed at basal nodes and flowering shoots are formed at upper nodes.

*Plant height.*—About 25 to 30 cm.

*Plant width.*—About 42 cm.

*Leaves.*—Arrangement: Simple, alternate. Developing leaves, length: About 5 to 6 cm. Developing leaves, width: About 5 to 6 cm. Fully expanded leaves, length: About 16 to 19 cm. Fully expanded leaves, width: About 14 to 16 cm. Shape: Asymmetrical, more or less reniform. Apex: Acuminate. Base: Cordate. Margin: Doubly serrate. Texture: Slightly pubescent. Venation pattern: Palmate. Color: Developing and fully expanded leaves, upper surface: Darker than 147A to 139A. Developing and fully expanded leaves, lower surface: 191A to 191B. Venation, upper and lower surfaces: 146C. Petiole length: About 2 to 8 cm. Petiole texture, upper and lower surfaces: Pubescent. Petiole color, upper and lower surfaces: 145A slightly overlain with 181A.

Flower description:

*Flowering habit.*—Double flowers with numerous tepals arranged in axillary cymes. Usually eight to ten flowers per cyme. Many cymes in flower simultaneously. Flowers positioned above and beyond the foliage.

*Natural flowering season.*—Plants will flower year around regardless of nyctoperiod, however plants flower earlier and more abundantly from mid-February until November in the Northern Hemisphere. Flowering continuous.

*Flowers.*—Shape: Rounded. Diameter: About 5.5 to 7 cm. Depth (height): About 2.5 cm.

*Flower buds.*—Length: About 1.2 to 1.6 cm. Diameter: About 1.3 to 1.8 cm. Color: 48A.

*Tepals.*—Arrangement: Rosette. Shape: Rounded flabellate. Apex: Rounded. Margin, outer and inner tepals: Slightly crenate. Quantity per flower: Usually about 22 per flower. Size, outer tepals: Length: About 3.3 to 3.6 cm. Width: About 3.7 to 4.2 cm. Size, inner tepals: Length: About 1 to 1.3 cm. Width: About 1.1 to 1.5 cm. Texture: Smooth, glabrous; satiny. Color: When opening, upper and lower surfaces: Center and towards base, 52A; towards the margin, 49C. Fully opened, upper surface: Center and towards base, 52A; towards the margin, 49D. Fully opened, lower surface: Center and towards base, 47C; towards the margin, 49D.

*Flower bracts.*—Arrangement: Two, opposite. Shape: Broadly cordate. Apex: Apiculate. Margin: Serrate. Texture: Smooth, glabrous. Color, upper and lower surfaces: 146B.

*Peduncles.*—Angle: Erect. Length: About 4 to 6 cm. Texture: Slightly pubescent. Color: Close to 180C to 180D.

*Pedicels.*—Angle: Erect. Length: About 2 to 3 cm. Texture: Glabrous. Color: 152B.

*Reproductive organs.*—Stamens: None observed. Pistils: None observed.

*Seed/fruit.*—Seed and fruit production has not been observed as reproductive organs are not formed.

Postproduction longevity:

*Individual flowers.*—Generally about two to three weeks.

*Whole plants.*—About six weeks under interior conditions.

Disease/pest resistance: Resistance to pathogens and pests common to Begonia has not been observed.

It is claimed:

1. A new and distinct cultivar of Begonia plant named 'Boriasko', as illustrated and described.

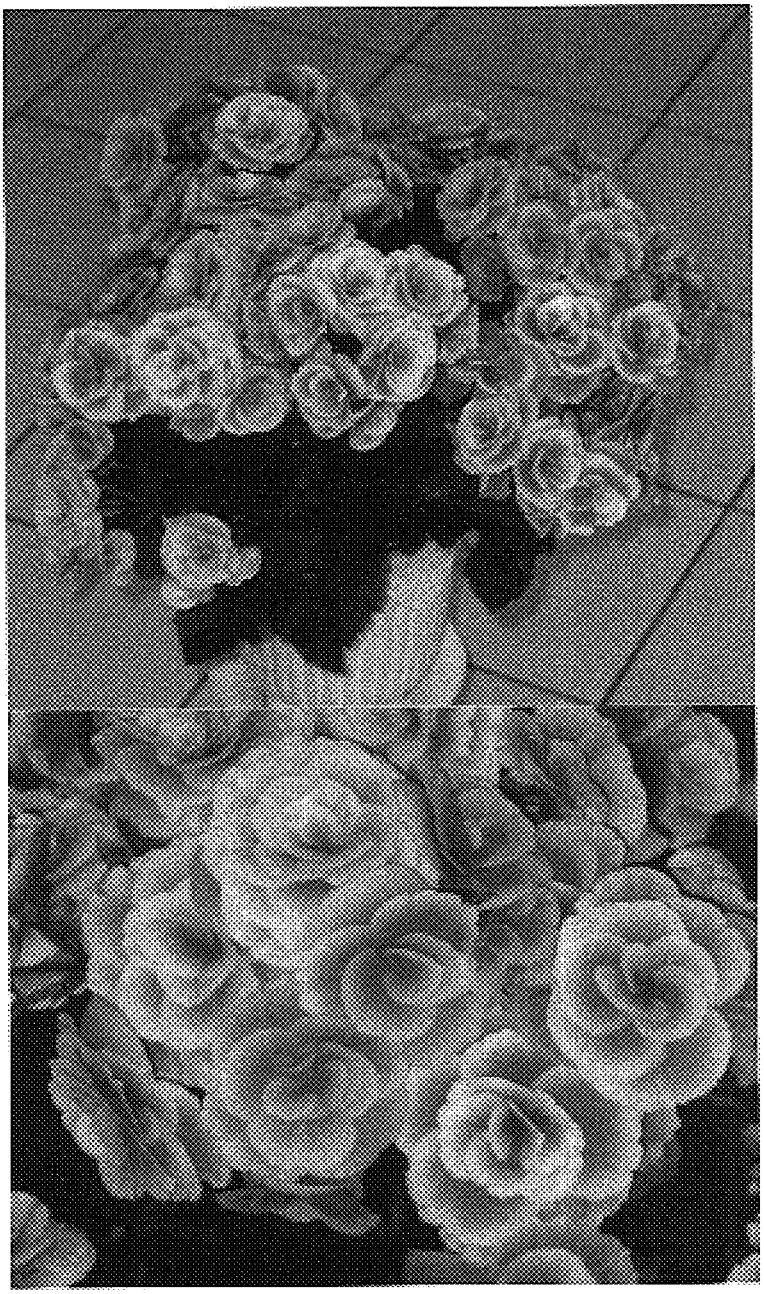

* * * * *